(12) United States Patent
Montaldo et al.

(10) Patent No.: US 7,857,762 B2
(45) Date of Patent: Dec. 28, 2010

(54) METHOD OF GENERATING A PREDETERMINED WAVE FIELD

(75) Inventors: Gabriel Montaldo, Paris (FR); Mathias Fink, Meudon (FR); Mickaël Tanter, Paris (FR)

(73) Assignee: Super Sonic Imagine, Aix-en-Provence (FR)

( * ) Notice: Subject to any disclaimer, the term of this patent is extended or adjusted under 35 U.S.C. 154(b) by 1553 days.

(21) Appl. No.: 10/517,047

(22) PCT Filed: May 28, 2003

(86) PCT No.: PCT/FR03/01617
§ 371 (c)(1),
(2), (4) Date: Jul. 27, 2005

(87) PCT Pub. No.: WO03/101302
PCT Pub. Date: Dec. 11, 2003

(65) Prior Publication Data
US 2005/0273008 A1 Dec. 8, 2005

(30) Foreign Application Priority Data
Jun. 4, 2002 (FR) .................................. 02 06846

(51) Int. Cl.
*A61B 8/00* (2006.01)
*A61H 1/00* (2006.01)
*G01N 9/24* (2006.01)

(52) U.S. Cl. ............................ 600/437; 600/447; 601/2; 73/602; 455/39

(58) Field of Classification Search ................. 600/437, 600/447, 443; 601/2; 73/602, 626
See application file for complete search history.

(56) References Cited

U.S. PATENT DOCUMENTS

| 5,092,336 | A | * | 3/1992 | Fink | .......................... 600/443 |
| 5,431,053 | A | * | 7/1995 | Fink | .......................... 73/602 |
| 6,198,829 | B1 | * | 3/2001 | Fink et al. | ................. 381/71.12 |
| 7,101,337 | B2 | * | 9/2006 | Aubry et al. | ................. 600/447 |

FOREIGN PATENT DOCUMENTS

WO    WO-03/101302 A1    12/2003

* cited by examiner

*Primary Examiner*—Eric F Winakur
*Assistant Examiner*—Katherine L Fernandez
(74) *Attorney, Agent, or Firm*—Marshall, Gerstein & Borun LLP

(57) ABSTRACT

The invention relates to a method of generating a predetermined objective wave field in a medium using a first network of transducers T1-Tn). The inventive method consists in first using each transducer i of the first network to emit an approximation of the signal ei(t). Subsequently, each transducer of a second network of transducers (T'1-T'm) is used to emit an error signal corresponding to the time reversal of the difference between the signals captured from said first emission and objective signals. Finally, approximation ei(t) is corrected by subtracting the time reversal of the signal captured by each transducer i using the error signal.

8 Claims, 1 Drawing Sheet

METHOD OF GENERATING A PREDETERMINED WAVE FIELD

Figure 1:
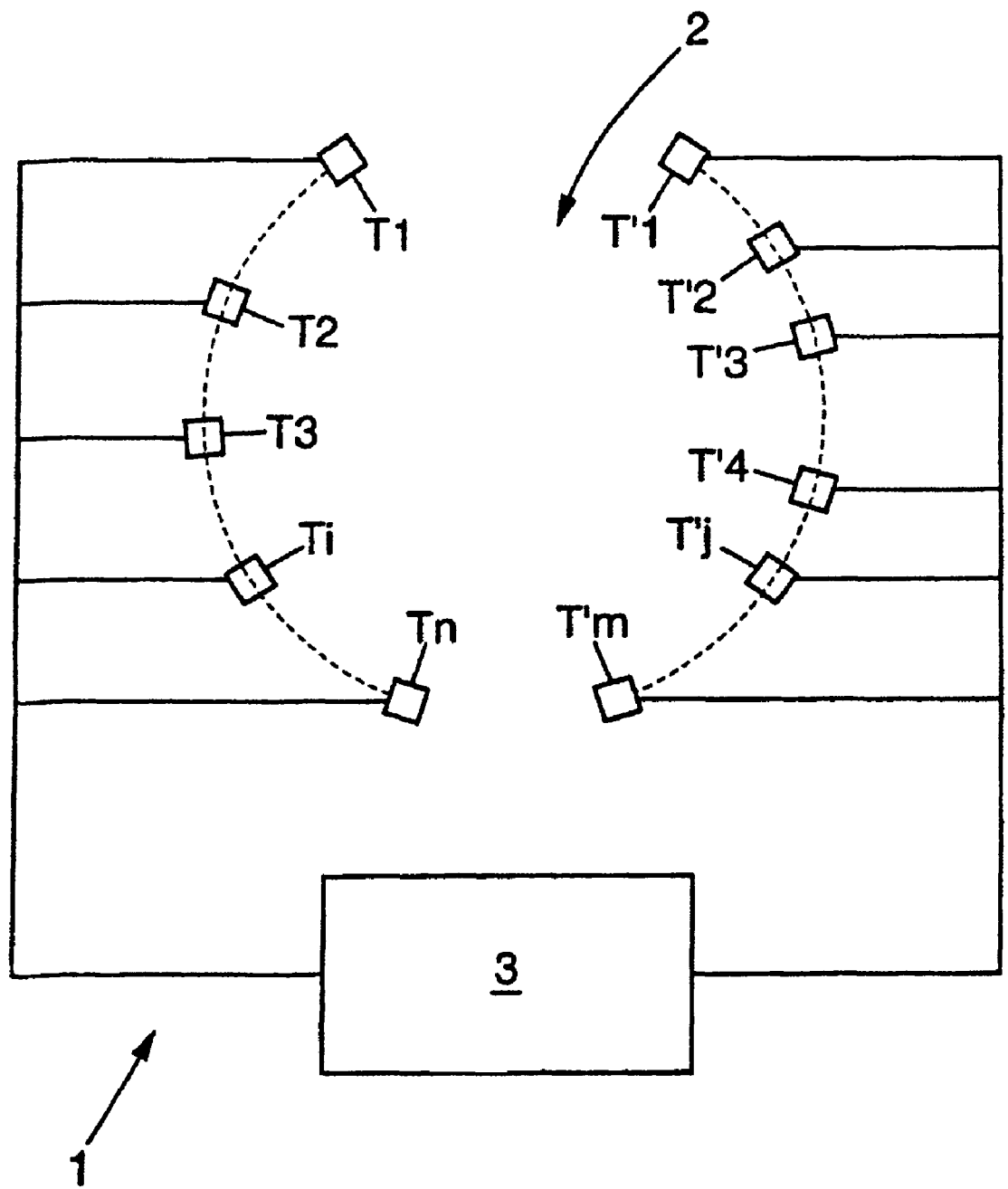

The present invention pertains to methods for generating predetermined wave fields in a medium.

The wave field in question can consist of a wave pulse focused at one or more points of the medium, or it may involve a more complex spatio-temporal field.

More particularly, the invention relates to a method for generating a predetermined objective wave field in a medium (homogeneous or heterogeneous) by means of a first network comprising at least one transducer, this method comprising a learning step in the course of which signals $ei(t)$ to be emitted by each transducer i of the first network so as to generate said predetermined wave field in the medium are determined by transmitting waves in the medium between the first network and a second network comprising at least one transducer (the second network may possibly comprise transducers in common with the first network).

Document WO-A-02/32316 describes an example of such a method, in which the abovementioned learning step makes it possible to determine signals to be applied to the transducers of the first network so as to focus a wave pulse respectively on each transducer of the second network, thereby subsequently making it possible to determine how to focus wave pulses at other points of the medium so as to image this medium by ultrasound waves. This known method is entirely satisfactory from the standpoint of its results; however, it does require considerable means of calculation and moreover involves fairly lengthy calculation times in the course of the learning step.

The present invention is aimed in particular at alleviating these drawbacks.

For this purpose, according to the invention, a method of the kind in question is characterized in that the learning step comprises the following correction sequence:

(a) making each transducer i of the first network simultaneously emit a signal $ei(t)$ determined in advance (these signals $ei(t)$ may initially be predetermined or previously determined by experiment as described hereafter, or these signals may result from step (g) hereinbelow an earlier iteration of the correction sequence) and making it possible to generate a real wave field much like the objective wave field in the medium, this objective wave field corresponding to an objective signal $oj(t)$ for each transducer j of the second network, (b) making each transducer j of the second network capture a signal $rj(t)$ resulting from the wave field generated by the signals $ei(t)$, (c) determining a time reversed difference signal $dj(-t)$ for each transducer j of the second network, $dj(-t)$ being the time reversal of the difference $dj(t)=rj(t)-oj(t)$, (d) making each transducer j of the second network simultaneously emit the time reversed difference signal $dj(-t)$, (e) making each transducer i of the first network capture a signal $c'i(t)$ based on the waves generated by the time reversed difference signals $dj(-t)$, (f) determining a correction signal $ci(t)=\beta \cdot c'i(-t)$ for each transducer i of the first network, $c'i(-t)$ being the time reversal of the captured signal $c'i(t)$ and $\beta$ being a positive nonzero real number chosen in such a way that $\beta < (\|\vec{e}\| \cdot \|\vec{d}\|)/(\|\vec{r}\| \cdot \|\vec{c'}\|)$ where $\vec{e}=[ei(t)]$, $\vec{d}=[dj(t)]$, $\vec{r}=[rj(t)]$, $\vec{c'}=[c'i(t)]$ and $\|\ \|$ designates a vector norm, (g) correcting the signal $ei(t)$ by subtracting $ci(t)$ therefrom.

By virtue of these arrangements, it is possible to generate the objective wave field very accurately, after one or more iterations of the correction sequence, even in a very dissipative and/or heterogeneous propagation medium.

In preferred embodiments of the invention, recourse may possibly be had moreover to one and/or other of the following arrangements:

the correction sequence is repeated several times;

the correction sequence is preceded by an initial step in the course of which a first value of the signal $ei(t)$ is determined experimentally for each transducer i of the first network;

in the course of the initial step, the time reversal $oj(-t)$ of the objective signal is determined for each transducer of the second network, each transducer j of the second network is made to emit said time reversal $oj(-t)$ of the objective signal, each transducer i of the first network is made to capture a signal $e'i(t)$ resulting from the wave field generated by the signals $dj(-t)$, and the signal $ei(t)=e'i(-t)$ is determined for each transducer of the first network, $e'i(-t)$ being the time reversal of the signal $e'i(t)$;

the vector norm is defined as follows: $\|\vec{x}\|=\|[x_m(t)]\|=\mathrm{Max}(|x_m(t)|)$, where $|x_m(t)|$ designates the amplitude of the signal $x_m(t)$;

the wave field is an acoustic wave field;

the wave field is an electromagnetic wave field;

the waves are generated by a telecommunication system.

Other characteristics and advantages of the invention will become apparent in the course of the following description of one of its embodiments, given by way of nonlimiting example, with regard to the appended drawing.

In the drawing

FIG. 1 is a basic diagram representing an exemplary device allowing implementation of the invention.

The wave generation device 1 represented in the drawing may in particular be:

a device for generating acoustic waves, in which case it may pertain for example to an ultrasound imaging device, to a sound system device, to an active anti-noise device, to an ultrasound therapy device (for example, lithotrity), or to a communication device, in particular an underwater device based on acoustic waves, or, as the case may be, a device for generating electromagnetic waves, in which case it may pertain to a telecommunications device.

The device 1 is intended to generate waves in a medium 2, which depending on the case, may be:

a part of a human or animal body to be imaged or to be treated (ultrasound medical imaging or ultrasound therapy), a part of an object to be imaged (ultrasound industrial imaging), the underwater or underground medium (telecommunications based on acoustic pathway), a public or private place (sound system or active anti-noise system), a part of the earth's surface together with the corresponding bottom layers of the atmosphere (radio telecommunications between fixed bases and mobiles), the earth's surface and the atmosphere including its top layers (radio-based long-distance terrestrial telecommunications or radio telecommunications between the earth and one or more satellites), etc.

In the various applications mentioned above, it is necessary to be able to generate one or more predetermined objective wave fields in the medium 2 with the greatest possible precision, for example so as to be able to focus the waves emitted by a first network of transducers T1, T2 . . . Tn at one or more points of the medium 2 or as the case may be to generate more complex wave fields.

The benefit of being able to perform high-precision focusing may for example be to produce an image of a part of the medium 2 with high precision, or to selectively destroy a part of the medium 2 (ultrasound therapy), and also to send one or more messages to specific sites of the medium and not within the remainder of the medium 2 (either in a desire for discretion, or in a desire to avoid interference between the various messages and thus to allow an increase in the telecommunications throughput).

The first network comprises a number n at least equal to 1 (advantageously at least equal to 2) of transducers T1-Tn capable of emitting and of receiving waves, for example ultrasound waves.

The signals $ei(t)$ which must be emitted by the transducers Ti to obtain the predetermined objective wave field or fields, are obtained in the course of a learning step, in the course of which a second network of transducers T'1-T'm is used.

This second network comprises a number n at least equal to 1 (advantageously at least equal to 2) of transducers T'1-T'm of the same type as the transducers T1-Tn.

This second network may be distinct from the first network T1-Tn, and be put in place in the medium 2 only in the course of the learning step, and then removed.

It would however be possible to imagine implementing the method of the present invention with a set of transducers remaining in place permanently in the medium, certain of these transducers serving to constitute the first network of transducers and others of these transducers serving to constitute the second network of transducers during the learning phase. At least certain transducers could moreover be common to the first and second networks or else belong either to the first network, or to the second network depending on the objective wave field that one seeks to obtain (and in particular depending on the point of the medium 2 onto which one seeks to focus the waves emitted).

The various transducers T1-Tn, T'1-T'm are controlled by an electronic control device 3 which will not be described in detail here. This control device may for example be identical or similar to the control device described in the document WO-A-02/32316 mentioned above when the device 1 is an imaging device or ultrasound acoustic therapy device.

The signals $ei(t)$ determined in the course of the learning step for each transducer Ti of the first network make it possible for example to generate in the medium 2 a wave field focused uniquely at a point at which one of the transducers of the second network is situated, for example the transducer T'1.

This learning step may of course be repeated for each of the transducers T'1-T'm of the second network, in such a way as to determine on each occasion signals $ei(t)$ making it possible to focus the wave field on any one of the points at which one of the transducers T'j of the second network is situated.

In all typical cases, in the course of one and the same learning step, the signals $ei(t)$ which have to be emitted by the transducers Ti of the first network so as to obtain objective signals $oj(t)$ corresponding to the objective wave field at the level of each transducer T'j of the second network are determined.

The control device 3 may possibly have in memory, in advance, initial values of the signals $ei(t)$ making it possible to obtain the desired wave field approximately.

However, in a preferred embodiment of the invention, these initial values of the signals $ei(t)$ are determined in the course of an initial step in which:

the transducers T'j of the second network are made to simultaneously emit signals $oj(-t)$, resulting from the time reversal of the objective signals $oj(t)$ (in the case where the objective signals $oj(t)$ consist either of simple pulses of $t=0$, or of flat signals, this step amounts simply to making the transducers T'j emit the objective signals $oj(t)$, the transducers Ti of the first network are made to capture signals $e'i(t)$ resulting from the wave field generated by the signals $oj(-t)$, and the initial value $ei(t)$ is determined by time reversal of the signals $e'i(t)$ mentioned above: $ei(t)=e'i(-t)$.

Once the initial value of the signal $ei(t)$ has been determined for each transducer T1 of the first network, one or more iterations of the following correction sequence are carried out:

(a) the various transducers Ti of the first network are made to simultaneously emit the signals $ei(t)$, (b) the various transducers T'j of the second network are made to capture signals $rj(t)$ resulting from the wave field generated by the signals $ei(t)$, (c) a time reversed difference signal $dj(-t)$ is determined for each transducer j of the second network, $dj(-t)$ being the time reversal of the difference $dj(t)=rj(t)-oj(t)$, (d) each transducer j of the second network is made to simultaneously emit the time reversed difference signal $dj(-t)$, (e) each transducer i of the first network is made to capture a signal $c'i(t)$ based on the waves generated by the time reversed difference signals $dj(-t)$, (f) a correction signal $ci(t)=\beta \cdot c'i(-t)$ is determined for each transducer i of the first network, $c'i(-t)$ being the time reversal of the captured signal $c'i(t)$ and $\beta$ being a positive nonzero real number chosen in such a way that $\beta < (\|\vec{e}\| \cdot \|\vec{d}\|)/(\|\vec{r}\| \cdot \|\vec{c}\|)$ where $\vec{e}=[ei(t)]$, $\vec{d}=[dj(t)]$, $\vec{r}=[rj(t)]$, $\vec{c}'=[c'i(t)]$ and $\|\ \|$ designates a vector norm (for example such as $\|\vec{x}\|=\|[x_m]\|=\mathrm{Max}(|x_m|)$, where $|x_m(t)|$ designates the amplitude of the signal $x_m(t)$). The value of $\beta$ defined hereinabove (generally greater than 1) allows the correction process to converge very rapidly toward signals $ei(t)$ complying with the objective sought, but the coefficient $\beta$ could also be taken equal to 1 without thereby departing from the scope of the invention, (g) correcting the signal $ei(t)$ by subtracting $ci(t)$ therefrom.

At the following iteration of the correction sequence, the value of the signal $ei(t)$ used in step (a) is thereafter that previously determined in step (g) of the correction sequence described hereinabove.

Experience shows that the correction process converges very rapidly, in a few milliseconds, even in a very dissipative and/or heterogeneous medium.

This rapid convergence, which moreover does not require heavyweight means of calculation, allows the system, as the case may be, to adapt in real time to modifications of the medium when the medium is changing, this being the case in particular in acoustic-based or radio-based telecommunications applications. In this case, the second network of transducers will not be removed after the starting learning step or steps, but will on the contrary be left in place so as to be able to repeat the learning step or steps, at regular or irregular time intervals.

It will be noted that throughout the learning process explained hereinabove, the signals emitted are given to within (nonzero) constant multiplicative coefficients.

Once the learning step or steps have terminated, the wave generation device 1 is capable of generating one or more predetermined wave fields in the medium 2 with very high precision.

For example, should several learning steps have been carried out, making it possible to precisely generate a pulse located uniquely at a point occupied by a transducer T'j of the second network, it is thereafter possible:

in imaging applications, to generate pulses located at any point of the medium 2 (by generating signals Ei(t) obtained either by simple methods of interpolation between the emission signals ei(t)$_j$ making it possible to focus the waves respectively on several transducers j of the second network, or by more complex methods such as those described for example in the document WO-A-02/32316 mentioned above), in ultrasound therapy applications, to generate a wave pulse of large amplitude at a particular point of the medium intended to be destroyed, this particular point possibly corresponding either to the location of one of the transducers T'j of the second network, or to a different point of the medium 2, in which case the signals making it possible to generate this pulse are determined as explained in the previous paragraph, in telecommunications applications, to generate an information-carrying signal at a point of the medium 2 (as in the previous two paragraphs, this point of the medium 2 may be one of the points occupied by the transducers of the second network or another point of the medium, in which case the signals to be emitted Ei(t) are determined by interpolation or by more complex methods such as those described in the document WO-A-02/32316 on the basis of the various signals ei(t)$_j$ making it possible to focus, the waves on the points occupied by the transducers Tj of the second network), this information-carrying signal being obtained by making the transducers Ti emit signals Si(t)=Ei(t)⊗S(t) equal to the convolution product of the signals Ei(t), with the information-carrying signal S(t) which must be transmitted to the desired point.

The invention claimed is:

1. A method of generating a predetermined objective wave field in a medium by a means of a first network comprising a plurality of transducers and a second network comprising a plurality of transducers, the method comprising a learning step in which signals ei(t) to be emitted by each transducer i of the first network so as to generate said predetermined objective wave field in the medium are determined by transmitting waves in the medium between the first network and the second network wherein the learning step comprises the following correction sequence:

(a) making each transducer i of the first network simultaneously emit a signal ei(t) determined in advance for generating a real wave field corresponding to the predetermined objective wave field in the medium, the predetermined objective wave field corresponding to an objective signal oj(t) for each transducer j of the second network, (b) making each transducer j of the second network capture a signal rj(t) resulting from the real wave field generated by the signals ei(t), (c) determining a time reversed difference signal dj(−t) for each transducer j of the second network, dj(−t) being the time reversal of the difference dj(t)=rj(t)−oj(t), (d) making each transducer j of the second network simultaneously emit the time reversed difference signal dj(−t), (e) making each transducer i of the first network capture a signal c'i(t) based on the waves generated by the time reversed difference signals dj(−t), determining a correction signal ci(t)=β·c'i(−t) for each transducer i of the first network, c'i(−t) being the time reversal of the captured signal c'i(t) and β being a positive nonzero real number chosen in such a way that $\beta < (\|\vec{e}\| \cdot \|\vec{d}\|)/(\|\vec{r}\| \cdot \|\vec{c}'\|)$ where $\vec{e}=[ei(t)]$, $\vec{d}=[dj(t)]$, $\vec{r}=[rj(t)]$, $\vec{c}'=c'i(t)]$ and $\|\ \|$ designates a vector norm.

2. The method as claimed in claim 1, in which the correction sequence is repeated several times.

3. The method as claimed in any one of the preceding claims, wherein the correction sequence is preceded by an initial step in the course of which a first value of the signal ei(t) is determined experimentally for each transducer i of the first network.

4. The method as claimed in claim 3, wherein in the initial step:

the time reversal oj(−t) of the objective signal is determined for each transducer of the second network, each transducer j of the second network is made to emit said time reversal oj(−t) of the objective signal, each transducer i of the first network is made to capture a signal e'i(t) resulting from the wave field generated by the signals oj(−t), and the signal ei(t)=e'i(−t) is determined for each transducer of the first network, e'i(−t) being the time reversal of the signal e'i(t).

5. The method as claimed in claim 1, in which the vector norm is defined as follows:

$\|\vec{x}\| = \|[x_m(t)]\| = \text{Max}(|x_m(t)|)$, where $|x_m(t)|$ designates the amplitude of the signal $x_m(t)$.

6. The method as claimed in claim 1, wherein the real wave field is an acoustic wave field.

7. The method as claimed in claim 1, wherein the real wave field is an electromagnetic wave field.

8. The method as claimed in claim 1, wherein the waves transmitted in the medium are generated by a telecommunication system.

* * * * *